United States Patent
Wang et al.

(10) Patent No.: US 10,449,272 B2
(45) Date of Patent: Oct. 22, 2019

(54) HYDROGEL COMPOSITION AND METHOD FOR USING THE SAME

(71) Applicant: Industrial Technology Research Institute, Hsinchu (TW)

(72) Inventors: Yu-Chi Wang, New Taipei (TW); Hsin-Hsin Shen, Zhudong Township (TW); Chin-Fu Chen, New Taipei (TW); Meng-Yow Hsieh, Taipei (TW); Sen-Lu Chen, Zhunan Township (TW); Yu-Bing Liou, Hsinchu (TW); Tsai-Yu Lin, Taipei (TW); Pei-Shan Li, Taipei (TW); Wei-Lin Yu, Zhubei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 15/294,047

(22) Filed: Oct. 14, 2016

(65) Prior Publication Data

US 2017/0106125 A1 Apr. 20, 2017

Related U.S. Application Data

(60) Provisional application No. 62/242,706, filed on Oct. 16, 2015.

(30) Foreign Application Priority Data

Oct. 7, 2016 (TW) .............................. 105132523 A

(51) Int. Cl.
*A61L 31/04* (2006.01)
*A61L 31/14* (2006.01)

(52) U.S. Cl.
CPC ........... *A61L 31/145* (2013.01); *A61L 31/041* (2013.01); *A61L 31/14* (2013.01); *A61L 2400/06* (2013.01)

(58) Field of Classification Search
CPC ....... A61L 31/145; A61L 31/041; A61L 31/14
See application file for complete search history.

(56) References Cited

U.S. PATENT DOCUMENTS

| | | | |
|---|---|---|---|
| 5,529,987 A | 6/1996 | Gallina | |
| 5,643,591 A | 7/1997 | Mehra et al. | |
| 6,471,993 B1 * | 10/2002 | Shastri | A61K 9/1647 424/422 |
| 8,133,513 B2 | 3/2012 | Hayashi et al. | |
| 8,211,959 B2 | 7/2012 | Shen et al. | |
| 8,815,277 B2 | 8/2014 | Park et al. | |
| 8,859,716 B2 | 10/2014 | Bowman et al. | |
| 2002/0193812 A1 | 12/2002 | Patel et al. | |
| 2004/0147466 A1 | 7/2004 | Barman et al. | |
| 2004/0191900 A1 * | 9/2004 | Mizuno | A61L 27/24 435/366 |
| 2008/0200948 A1 | 8/2008 | Utecht et al. | |
| 2010/0166863 A1 | 7/2010 | Shen et al. | |
| 2011/0008442 A1 | 1/2011 | Zawko et al. | |
| 2012/0100103 A1 | 4/2012 | Park et al. | |
| 2014/0038826 A1 | 2/2014 | Anseth et al. | |
| 2014/0142191 A1 | 5/2014 | De La Zerda et al. | |
| 2014/0178964 A1 | 6/2014 | Mooney et al. | |
| 2014/0187591 A1 | 7/2014 | Shen et al. | |

FOREIGN PATENT DOCUMENTS

| TW | 201024338 A1 | 7/2010 |
|---|---|---|
| TW | 201200173 A1 | 1/2012 |
| TW | I374903 B1 | 10/2012 |
| TW | 201438770 A | 10/2014 |
| TW | I499436 B | 9/2015 |

OTHER PUBLICATIONS

Taiwanese Office Action and Search Report, dated Feb. 10, 2017, for Taiwanese Application No. 105132523.

* cited by examiner

*Primary Examiner* — Alma Pipic
(74) *Attorney, Agent, or Firm* — Birch, Stewart, Kolasch & Birch, LLP

(57) ABSTRACT

The present disclosure provides a hydrogel composition including: a hydrogel having a structure represented by Formula (I) or Formula (II) shown as follows: A-B-BOX-B-A, Formula (I); B-A-B-(BOX-BAB)n-BOX-B-A-B, Formula (II), wherein A is a hydrophilic polyethylene glycol polymer, B is a hydrophobic polyester polymer, BOX is a bifunctional group monomer of 2,2'-Bis(2-oxazoline) for coupling di-block of A-B or tri-block of B-A-B, and n is an integer greater than or equal to 0; and an anti-adhesion additive, wherein the anti-adhesion additive comprises a carbohydrate, a nitrogen-containing cyclic compound, a polymer or a combination thereof.

10 Claims, 1 Drawing Sheet

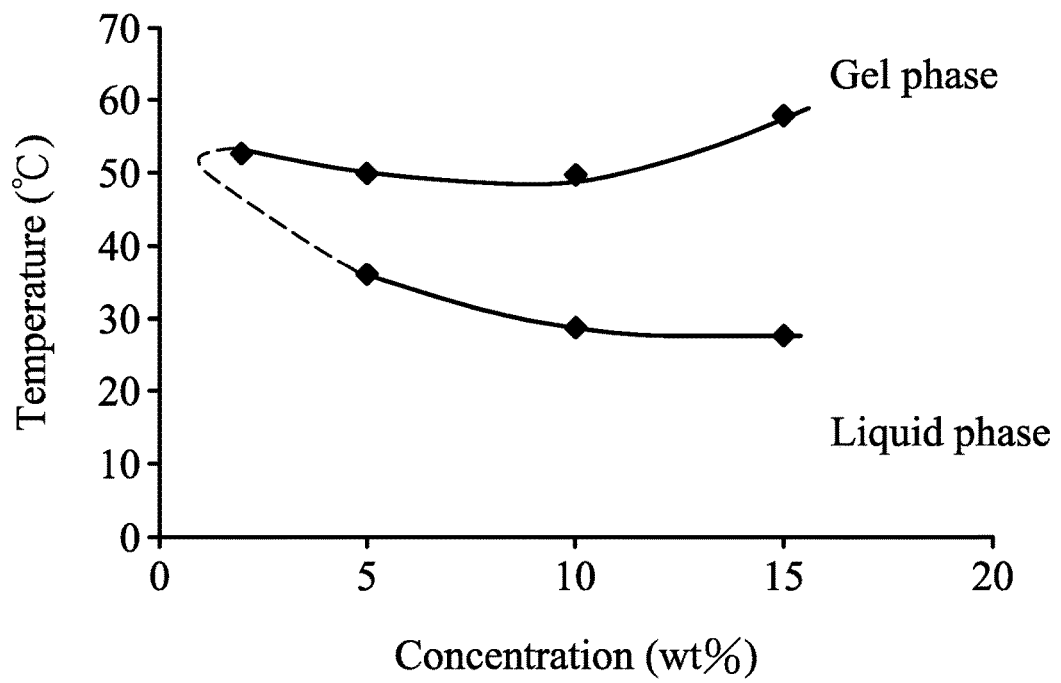

HYDROGEL COMPOSITION AND METHOD FOR USING THE SAME

CROSS REFERENCE TO RELATED APPLICATION

This application claims the benefit of U.S. Provisional Application No. 62/242,706, filed on Oct. 16, 2015, the entirety of which is incorporated by reference herein.

The present application is also based on, and claims priority from, Taiwan Application Serial Number 105132523, filed on Oct. 7, 2016, the disclosure of which is hereby incorporated by reference herein in its entirety.

TECHNICAL FIELD

The technical field relates to a hydrogel composition and a method for using the same.

BACKGROUND

In recent years, degradable hydrogel material has been widely applied in medical treatments. For example, it can be used as bone cement, a releasing vehicle for implant drugs, a substrate for minimally invasive surgery or drug delivery, etc. However, in a clinical application and commercialization process, the problems with hydrogel material need to be solved. These problems include its short preservation time, low stability, and inconvenience for the users due to its long re-dissolved time (a few hours or a few days is required).

However, at present, most anti-adhesion products exist in the form of film, causing inconvenience and limiting the application of the anti-adhesion products. Film-type products cannot be used for minimally invasive surgery since these film-type products cannot be placed a specific area of the affected region precisely enough, and in a minimally invasive manner. Gel-form or liquid-form products can solve the problem mentioned above, but they still have problems in that they cannot be affixed as they tend to flow.

Therefore, easy operation, good anti-adhesion effect and long preservation time are all development objectives for hydrogel materials.

Accordingly, what is needed is a novel temperature-sensitive hydrogel composition which is more convenient to be re-dissolved, preserved, and used, and which is capable of effectively decreasing adhesion incidence.

SUMMARY

The present disclosure provides a hydrogel composition comprising: a hydrogel having a structure represented by Formula (I) or Formula (II) shown as follows: A-B-BOX-B-A, Formula (I); B-A-B-(BOX-BAB)n-BOX-B-A-B, Formula (II), wherein, A is a hydrophilic polyethylene glycol polymer, B is a hydrophobic polyester polymer, BOX is a bifunctional group monomer of 2,2'-Bis(2-oxazoline) for coupling di-block of A-B or tri-block of B-A-B, and n is an integer greater than or equal to 0; and an anti-adhesion additive, wherein the anti-adhesion additive comprises a carbohydrate, a nitrogen-containing cyclic compound, a polymer or a combination thereof.

The present disclosure further provides a method for using a hydrogel composition, comprising: dissolving the hydrogel composition as claimed in claim 1 in water at a first temperature to form a liquid; and applying the liquid to a substrate, wherein the substrate has a second temperature, and the liquid forms into a gel at the second temperature.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein:

FIG. 1 is a phase diagram of liquid-gel phase of a hydrogel composition obtained from one embodiment of the present disclosure.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

According to the present disclosure, a hydrogel composition is provided. The hydrogel composition comprises a hydrogel having a structure represented by Formula (I) or Formula (II) shown as follows:

A-B-BOX-B-A,  Formula (I);

B-A-B-(BOX-BAB)n-BOX-B-A-B,  Formula (II), wherein, A is a hydrophilic polyethylene glycol polymer, B is a hydrophobic polyester polymer, BOX is a bifunctional group monomer of 2,2'-Bis(2-oxazoline) for coupling di-block of A-B or tri-block of B-A-B, and n is an integer greater than or equal to 0.

The hydrogel composition also comprises an anti-adhesion additive, wherein the anti-adhesion additive comprises a carbohydrate, a nitrogen-containing cyclic compound, a polymer or a combination thereof. Based on one embodiment of the present disclosure, the polymer may be a hydrophilic polymer although the polymer herein is not a hydrogel with a structure represented by Formula (I) or Formula (II). The polymer block A comprises polyethylene glycol (PEG) or methoxy-poly(ethylene glycol) (mPEG). The polymer block B, for example, comprises poly(lactide-co-glycolide) (PLGA), poly(propionic-co-lactic) (PPLA), poly(valeric-co-lactic) (PVLA) or poly(caproic-co-lactic) (PCLA).

Based on one embodiment of the present disclosure, the foregoing hydrogel composition consists of the hydrogel and the anti-adhesion additive. The weight percentage of the preceding anti-adhesion additive is 0.2-75 wt %, such as 0.3-70 wt % or 0.33-67 wt %, based on the total weight of the hydrogel composition.

According to one embodiment of the present disclosure, the foregoing carbohydrate comprises glucose, hyaluronic acid, carboxymethyl cellulose, etc., but it is not limited thereto. The weight percentage of the preceding carbohydrate is 0.2-75 wt %, such as 0.3-70 wt %, 0.33-67 wt % or 0.6-67 wt %, based on the total weight of the hydrogel composition. For example, the weight percentage of the glucose may be 0.33-5 wt % while the weight percentage of the hyaluronic acid may be 1-5 wt %, based on the total weight of the hydrogel composition.

According to one embodiment of the present disclosure, examples of the foregoing nitrogen-containing cyclic compound include polyvinylpyrrolidone (PVP), antibiotics (with a symmetrical structure), such as vancomycin, etc., but they are not limited thereto. The weight percentage of the preceding nitrogen-containing cyclic compound is 0.2-75 wt %, such as 0.3-70 wt %, 0.33-67 wt % or 3-67 wt %, based on the total weight of the hydrogel composition. The weight percentage of the vancomycin may be 3-16 wt %, such as 5-10 wt %, based on the total weight of the hydrogel composition. Moreover, the weight percentage of the polyvinylpyrrolidone may be 0.2-75 wt %, such as 3-67 wt %, based on the total weight of the hydrogel composition.

The polymer mentioned above may be a hydrophilic polymer comprising poly(acrylic) acid (PAA), poly(vinyl alcohol) (PVA), poly(ethylene glycol)diacrylate (PEGDA), collagen or gelatin, but it is not limited thereto. The weight percentage of the polymer is 0.2-75 wt %, such as 0.3-70 wt % or 0.33-67 wt %, based on the total weight of the hydrogel composition. The weight percentage of the poly(acrylic) acid (PAA) is 0.3-70 wt %, such as 0.3-60 wt %, based on the total weight of the hydrogel composition. The weight percentage of the poly(vinyl alcohol) (PVA) is 3-60 wt %, based on the total weight of the hydrogel composition. The weight percentage of the poly(ethylene glycol)diacrylate (PEGDA) is 3-70 wt %, based on the total weight of the hydrogel composition. The weight percentage of the collagen is 30-70 wt %, such as 40-60 wt %, based on the total weight of the hydrogel composition. The weight percentage of the gelatin is 30-70 wt %, such as 40-60 wt %, based on the total weight of the hydrogel composition.

The hydrogel composition mentioned above, for example, may be powder, and the particle size of the powder is between 0.1 µm and 1 mm. Based on another embodiment of the present disclosure, the hydrogel composition is dissolved in water or a phosphate buffered saline (PBS) to become a liquid at a first temperature, and the viscosity of the liquid is less than 100 Pa-s. Moreover, the preceding liquid formed by dissolving the hydrogel composition in water or a phosphate buffered saline (PBS) becomes a gel at a second temperature, and the viscosity range of the gel is between 100 Pa-s and 250 Pa-s (Metric=N/m2-sec).

The present disclosure provides a method for using a hydrogel composition. First, the hydrogel composition mentioned above is dissolved in water or a phosphate buffered saline (PBS) at a first temperature to form a liquid, and the first temperature is between 4° C. and 30° C., viscosity of the liquid is determined as less than 100 Pa-s by detecting an elastomer of a sample, shear modulus, and complex viscosity of a sample of the liquid through a rheometer. Then, the liquid is applied to a substrate, wherein the substrate has a second temperature, and the second temperature is between 30° C. and 55° C. to make the liquid form into a gel at the second temperature, and the viscosity range of the gel is between 200 Pa-s and 250 Pa-s. Fluids can be classified based on their viscosity. If the viscosity of a fluid is low, the fluid may belong to a liquid rather than a gel. If a hydrogel composition is in liquid form, when applied to an affected region, it will flow and cannot precisely remain at a specific part to achieve the purpose of isolation, anti-adhesion and protecting the affected region.

EXAMPLES

Preparation of Hydrogel

A di-block or tri-block copolymer obtained by copolymerizing a hydrophobic polymer with a hydrophilic polymer is provided, wherein the hydrophilic polymer comprises polyethylene glycol (PEG) or methoxy-poly(ethylene glycol) (mPEG) while the hydrophobic polymer comprises poly(lactide-co-glycolide) (PLGA), poly(propionic-co-lactic (PPLA), poly(valeric-co-lactic) (PVLA) or poly(caproic-co-lactic) (PCLA). According to some embodiments of the present disclosure, the biodegradable temperature-sensitive hydrogel copolymer comprises PEG-PLGA, PEG-PLGA-PEG, PLGA-PEG-PLGA or a combination thereof. The PEG mentioned above means a hydrophilic polyethylene glycol polymer, and may be poly(ethylene glycol) (PEG) or methoxy-poly(ethylene glycol) (mPEG). Molecular weight of the hydrophilic polyethylene glycol polymer may be between 350 and 2000 g/mol. The PLGA above means a hydrophobic poly(lactic-co-glycolic acid), and it may be a product of polymerizing or copolymerizing D,L-Lactide, D-Lactide, L-Lactide, D,L-Lactic acid, D-Lactic acid, L-Lactic acid, glycolide, β-propiolactone, δ-valerolactone, ε-caprolactone monomers, etc., and also may be a polymerized product obtained by optionally mixing the preceding monomers, wherein molecular weight of the hydrophobic poly(lactic-co-glycolic acid) may be between 1000 and 3500 g/mol.

Based on another embodiment of the present disclosure, the biodegradable copolymer has a structure represented by Formula (I) or Formula (II) shown as follows:

A-B-BOX-B-A,                                                             Formula (I);

B-A-B-(BOX-BAB)n-BOX-B-A-B,                  Formula (II), wherein, A is a hydrophilic polyethylene glycol polymer, B is a hydrophobic polyester polymer, BOX is a bifunctional group monomer of 2,2'-Bis(2-oxazoline) for coupling di-block of A-B or tri-block of B-A-B, and n is an integer greater than or equal to 0.

In addition to (poly(ethylene glycol) (PEG), the hydrophilic polyethylene glycol polymer mentioned by the present disclosure may also comprise methoxy-poly(ethylene glycol) (mPEG), and molecular weight of the hydrophilic polyethylene glycol polymer may be between 350 and 5000 g/mol. Furthermore, the hydrophobic polyester polymer may be a product of polymerizing or copolymerizing D,L-Lactide, D-Lactide, L-Lactide, D,L-Lactic acid, D-Lactic acid, L-Lactic acid, glycolide, β-propiolactone, δ-valerolactone, ε-caprolactone monomers, etc., and also may be a polymerized product obtained by optionally mixing the preceding monomers, such as poly(lactide-co-glycolide) (PLGA), poly(propionic-co-lactic (PPLA), poly(valeric-co-lactic) (PVLA) or poly(caproic-co-lactic) (PCLA), wherein molecular weight of the hydrophobic polyester polymer may be between 500 and 5000 g/mol. For example, the hydrophobic polyester polymer may be poly(lactide-co-glycolide) (PLGA) which is formed by copolymerizing poly(lactic acid) (PLA) and poly(glycolide acid) (PGA), wherein mole percent of poly(lactic acid) (PLA) is 50 mol %-90 mol % while mole percent of poly(glycolide acid) (PGA) is 10 mol %-50 mol %, based on the total mole of poly(lactic acid) (PLA) and poly(glycolide acid) (PGA).

According to one embodiment of the present disclosure, the end of the hydrophobic polyester polymer which is not linked to the polymer block A has an end capping/coupling functional group, wherein the hydrophobic polyester polymer is linked to BOX through the end capping/coupling functional group. The end capping/coupling functional group is a group derived from an end capping/coupling agent, wherein the end capping/coupling agent comprises an anhydride, such as succinic anhydride, maleic anhydride, phthalic anhydride, seB-Acic anhydride or another anhydride.

Hydrogel Preparation Example 1

First. 10.04 g mPEG (methoxy poly(ethylene glycol)) (molecular weight: 550 g/mole), 20 g Lactide and 5.64 g Glycolide were added to a reactor, sequentially, and the temperature of the reactor was raised slowly until the content in the reactor was dissolved, completely. The temperature was continuously raised to 160° C., and at the same time, 14.0 μl of a catalyst, Stannous 2-ethyl-Hexanoate, was added to the reactor for reacting for 8 hours (Lactide and Glycolide were copolymerized into poly(lactide-co-glycolide) (PLGA)). After the reaction was completed, 1.84 g Succinic anhydride (SA) (molecular weight: 100.07 g/mole) was added to the reactor. Next, after reacting for 4 hours, 1.28 g 2,2'-Bis(2-oxazoline) (BOX) (molecular weight: 140.14 g/mole) was added to the reactor. After the 2,2'-Bis (2-oxazoline) (BOX) was completely melted, a catalyst, stannous octoate, was added to the reactor for continuously reacting for 4 hours. The obtained product was precipitated by diethyl ether/n-hexane (volume ratio: 1:9) as a semi-transparent gel, and the remaining monomers were washed out three times. After that, the obtained product was vacuum-dried at 40° C. for 24 hours to obtain a BOX cross-linked di-block biodegradable copolymer hydrogel (mPEG-PLGA).

Preparation of Hydrogel Composition

Example 1

0.1 parts by weight of glucose (molecular weight: 180 g/mole) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (1). Next, the hydrogel composition (1) was tested to determine whether it was capable of gelling under 37° C. or not and the osmotic pressure range thereof was determined. The result is shown in Table 1.

Example 2

0.5 parts by weight of glucose (molecular weight: 180 g/mole) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (2). Next, the hydrogel composition (2) was tested to determine whether it was capable of gelling under 37° C. or not and the osmotic pressure range thereof was determined. It was observed that the hydrogel composition (2) was completely dissolved in water after being added to water for 10 minutes. The results are shown in Table 1.

Example 3

10 parts by weight of collagen (100 kDa-250 kDa) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (3). Next, the hydrogel composition (3) was tested to determine whether it was capable of gelling under 37° C. or not and the osmotic pressure range thereof was determined. It was observed that the hydrogel composition (3) was completely dissolved in water after being added to water for 10 minutes. The results are shown in Table 1.

Example 4

20 parts by weight of collagen (100 kDa-250 kDa) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (4). Next, the hydrogel composition (4) was tested to determine whether it was capable of gelling under 37° C. or not and the osmotic pressure range thereof was determined. It was observed that the hydrogel composition (4) was completely dissolved in water after being added to water for 10 minutes. The results are shown in Table 1.

Example 5

10 parts by weight of gelatin (90-300 g Bloom) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (5). Next, the hydrogel composition (5) was tested to determine whether it was capable of gelling under 37° C. or not and the osmotic pressure range thereof was determined. It was observed that the hydrogel composition (5) was completely dissolved in water after being added to water for 10 minutes. The results are shown in Table 1.

Example 6

20 parts by weight of gelatin (90-300 g Bloom) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (6). Next, the hydrogel composition (6) was tested to determine whether it was capable of gelling under 37° C. or not and the osmotic pressure range thereof was determined. It was observed that the hydrogel composition (6) was completely dissolved in water after being added to water for 10 minutes. The results are shown in Table 1.

Example 7

0.25 parts by weight of hyaluronic acid (molecular weight: 58 Da) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (7). Next, the hydrogel composition (7) was tested to determine whether it was capable of gelling under 37° C. or not and the osmotic pressure range thereof was determined. It was observed that the hydrogel composition (7) was completely dissolved in water after being added to water for 10 minutes. The results are shown in Table 1.

Example 8

0.5 parts by weight of hyaluronic acid (molecular weight: 100 Da) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (8). Next, the hydrogel composition (8) was tested to determine whether it was capable of gelling under 37° C. or not and the osmotic pressure range thereof was determined. It was observed that the hydrogel composition (8) was completely dissolved in water after being added to water for 10 minutes. The results are shown in Table 1.

Example 9

0.06 parts by weight of carboxymethyl cellulose (molecular weight: 250,000) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (9). Next, the hydrogel composition (9) was tested to determine whether it was capable of gelling under 37° C. or not and the osmotic pressure range thereof was determined. It was observed that the hydrogel composition (9) was completely dissolved in water after being added to water for 10 minutes. The results are shown in Table 1.

Example 10

0.13 parts by weight of carboxymethyl cellulose (molecular weight: 250,000) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (10). Next, the hydrogel composition (10) was tested to determine whether it was capable of gelling under 37° C. or not and the osmotic pressure range thereof was determined. It was observed that the hydrogel composition (10) was completely dissolved in water after being added to water for 10 minutes. The results are shown in Table 1.

Example 11

20 parts by weight of carboxymethyl cellulose (molecular weight: 7,000,000) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (11). Next, the hydrogel composition (11) was tested to determine whether it was capable of gelling under 37° C. or not and the osmotic pressure range thereof was determined. It was observed that the hydrogel composition (11) was completely dissolved in water after being added to water for 10 minutes. The results are shown in Table 1.

Example 12

30 parts by weight of carboxymethyl cellulose (molecular weight: 7,000,000) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (12). Next, the hydrogel composition (12) was tested to determine whether it was capable of gelling under 37° C. or not and the osmotic pressure range thereof was determined. It was observed that the hydrogel composition (12) was completely dissolved in water after being added to water for 10 minutes. The results are shown in Table 1.

Example 13

0.6 parts by weight of polyvinylpyrrolidone (PVP) (molecular weight: about 40,000-360,000) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (13). Next, the hydrogel composition (13) was tested to determine whether it was capable of gelling under 37° C. or not and the osmotic pressure range thereof was determined. It was observed that the hydrogel composition (13) was completely dissolved in water after being added to water for 10 minutes. The results are shown in Table 1.

Example 14

10 parts by weight of polyvinylpyrrolidone (PVP) (molecular weight: about 40,000-360,000) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (14). Next, the hydrogel composition (14) was tested to determine whether it was capable of gelling under 37° C. or not and the osmotic pressure range thereof was determined. It was observed that the hydrogel composition (14) was completely dissolved in water after being added to water for 10 minutes. The results are shown in Table 1.

Example 15

30 parts by weight of polyvinylpyrrolidone (PVP) (molecular weight: about 40,000-360,000) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (15). Next, the hydrogel composition (15) was tested to determine whether it was capable of gelling under 37° C. or not and the osmotic pressure range thereof was determined. It was observed that the hydrogel composition (15) was completely dissolved in water after being added to water for 10 minutes. The results are shown in Table 1.

Example 16

1 part by weight of vancomycin and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (16). Next, the hydrogel composition (16) was tested to determine whether it was capable of gelling under 37° C. or not and the osmotic pressure range thereof was determined. It was observed that the hydrogel composition (16) was completely dissolved in water after being added to water for 15 minutes. The results are shown in Table 1.

Example 17

1.25 parts by weight of vancomycin and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (17). Next, the hydrogel composition (17) was tested to determine whether it was capable of gelling under 37° C. or not and the osmotic pressure range thereof was determined. It was observed that the hydrogel composition (17) was completely dissolved in water after being added to water for 15 minutes. The results are shown in Table 1.

Example 18

1.5 parts by weight of vancomycin and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (18). Next, the hydrogel composition (18) was tested to determine whether it was capable of gelling under 37° C. or not and the osmotic pressure range thereof was determined. It was observed that the hydrogel composition (18) was completely dissolved in water after being added to water for 15 minutes. The results are shown in Table 1.

Example 19

0.05 parts by weight of poly(acrylic) acid (PAA) (molecular weight: about 2000) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (19). Next, the hydrogel composition (19) was tested to determine whether it was capable of gelling under 37° C. or not and the osmotic pressure range thereof was determined. It was observed that the hydrogel composition (19) was completely dissolved in water after being added to water for 10 minutes. The results are shown in Table 1.

Example 20

5 parts by weight of poly(acrylic) acid (PAA) (molecular weight: about 2000) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (20). Next, the hydrogel composition (20) was tested to determine whether it was capable of gelling under 37° C. or not and the osmotic pressure range thereof was determined. It was observed that the hydrogel composition (20) was completely dissolved in water after being added to water for 10 minutes. The results are shown in Table 1.

Example 21

10 parts by weight of poly(acrylic) acid (PAA) (molecular weight: about 3,000,000) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (21). Next, the hydrogel composition (21) was tested to determine whether it was capable of gelling under 37° C. or not and the osmotic pressure range thereof was determined. It was observed that the hydrogel composition (21) was completely dissolved in water after being added to water for 10 minutes. The results are shown in Table 1.

Example 22

20 parts by weight of poly(acrylic) acid (PAA) (molecular weight: about 3,000,000) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (22). Next, the hydrogel composition (22) was tested to determine whether it was capable of gelling under 37° C. or not and the osmotic pressure range thereof was determined. It was observed that the hydrogel composition (22) was completely dissolved in water after being added to water for 10 minutes. The results are shown in Table 1.

Example 23

0.6 parts by weight of poly(vinyl alcohol) (PVA) (molecular weight: about 2000-14,600) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (23). Next, the hydrogel composition (23) was tested to determine whether it was capable of gelling under 37° C. or not and the osmotic pressure range thereof was determined. It was observed that the hydrogel composition (23) was completely dissolved in water after being added to water for 10 minutes. The results are shown in Table 1.

Example 24

10 parts by weight of poly(vinyl alcohol) (PVA) (molecular weight: about 2000) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (24). Next, the hydrogel composition (24) was tested to determine whether it was capable of gelling under 37° C. or not and the osmotic pressure range thereof was determined. It was observed that the hydrogel composition (24) was completely dissolved in water after being added to water for 10 minutes. The results are shown in Table 1.

Example 25

30 parts by weight of poly(vinyl alcohol) (PVA) (molecular weight: about 14,600) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (25). Next, the hydrogel composition (25) was tested to determine whether it was capable of gelling under 37° C. or not and the osmotic pressure range thereof was determined. It was observed that the hydrogel composition (25) was completely dissolved in water after being added to water for 10 minutes. The results are shown in Table 1.

Example 26

0.05 parts by weight of poly(ethylene glycol)diacrylate (PEGDA) (molecular weight: about 100-6000) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (26). Next, the hydrogel composition (26) was tested to determine whether it was capable of gelling under 37° C. or not and the osmotic pressure range thereof was determined. It was observed that the hydrogel composition (26) was completely dissolved in water after being added to water for 5 minutes. The results are shown in Table 1.

Example 27

0.3 parts by weight of poly(ethylene glycol)diacrylate (PEGDA) (molecular weight: about 100-6000) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (27). Next, the hydrogel composition (27) was tested to determine whether it was capable of gelling under 37° C. or not and the osmotic pressure range thereof was determined. It was observed that the hydrogel composition (27) was completely dissolved in water after being added to water for 5 minutes. The results are shown in Table 1.

Example 28

0.5 parts by weight of poly(ethylene glycol)diacrylate (PEGDA) (molecular weight: about 100-6000) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (28). Next, the hydrogel composition (28) was tested to determine whether it was capable of gelling under 37° C. or not and the osmotic pressure range thereof was determined. It was observed that the hydrogel composition (28) was completely dissolved in water after being added to water for 5 minutes. The results are shown in Table 1.

Example 29

10 parts by weight of poly(ethylene glycol)diacrylate (PEGDA) (molecular weight: about 100-6000) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (29). Next, the hydrogel composition (29) was tested to determine whether it was capable of gelling under 37° C. or not and the osmotic pressure range thereof was determined. It was observed that the hydrogel composition (29) was completely dissolved in water after being added to water for 5 minutes. The results are shown in Table 1.

Example 30

30 parts by weight of poly(ethylene glycol)diacrylate (PEGDA) (molecular weight: about 100-6000) and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition (30). Next, the hydrogel composition (30) was tested to determine whether it was capable of gelling under 37° C. or not and the osmotic pressure range thereof was determined. It was observed that the hydrogel composition (30) was completely dissolved in water after being added to water for 5 minutes. The results are shown in Table 1.

TABLE 1

| Example | Anti-adhesion additive | Parts by weight | Hydrogel (parts by weight) | Gelling under 37° C. | Osmotic pressure range (mOsm/kg) |
|---|---|---|---|---|---|
| 1 | Glucose | 0.1 | 15 | Yes | ≤250 |
| 2 | | 0.5 | 15 | Yes | |
| 3 | Collagen | 10 | 15 | Yes | ≤350 |
| 4 | | 20 | 15 | Yes | |

TABLE 1-continued

| Example | Anti-adhesion additive | Parts by weight | Hydrogel (parts by weight) | Gelling under 37° C. | Osmotic pressure range (mOsm/kg) |
|---|---|---|---|---|---|
| 5 | Gelatin | 10 | 15 | Yes | ≤350 |
| 6 |  | 20 | 15 | Yes |  |
| 7 | Hyaluronic acid | 0.25 | 15 | Yes | ≤350 |
| 8 |  | 0.5 | 15 | Yes |  |
| 9 | Carboxymethyl | 0.06 | 15 | Yes | ≤150 |
| 10 | cellulose | 0.13 | 15 | Yes |  |
| 11 |  | 20 | 15 | Yes |  |
| 12 |  | 30 | 15 | Yes |  |
| 13 | Polyvinyl- | 0.6 | 15 | Yes | ≤150 |
| 14 | pyrrolidone | 10 | 15 | Yes |  |
| 15 | (PVP) | 30 | 15 | Yes |  |
| 16 | Vancomycin | 1 | 15 | Yes | ≤25 |
| 17 |  | 1.25 | 15 | Yes |  |
| 18 |  | 1.5 | 15 | Yes |  |
| 19 | Poly(acrylic) acid | 0.05 | 15 | Yes | ≤150 |
| 20 | (PAA) | 5 | 15 | Yes |  |
| 21 |  | 10 | 15 | Yes |  |
| 22 |  | 20 | 15 | Yes |  |
| 23 | Poly(vinyl | 0.6 | 15 | Yes | ≤150 |
| 24 | alcohol) (PVA) | 10 | 15 | Yes |  |
| 25 |  | 30 | 15 | Yes |  |
| 26 | Poly(ethylene | 0.05 | 15 | Yes | ≤200 |
| 27 | glycol)diacrylate | 0.3 | 15 | Yes |  |
| 28 | (PEGDA) | 0.5 | 15 | Yes |  |
| 29 |  | 10 | 15 | Yes |  |
| 30 |  | 30 | 15 | Yes |  |

Comparative Example 1

0.5 parts by weight of urea and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition. The highest osmotic pressure of the hydrogel composition was 450 (mOsm/kg).

Comparative Example 2

6 parts by weight of urea and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition. The highest osmotic pressure of the hydrogel composition was 600 (mOsm/kg).

Osmotic pressure influences cells, and a hydrogel with an osmotic pressure that is too high will result in serious effects on physiological tissues. Since urea itself will cause a very high osmotic pressure, even if the amount added is very low, it still causes that a hydrogel composition containing thereof has an osmotic pressure that is too high, and it cannot be used in clinical applications. According to Table 1, it is known that the hydrogel compositions containing different anti-adhesion additives mentioned in the present disclosure have the highest osmotic pressures not exceeding 350 (mOsm/kg). Accordingly, it is proved that the anti-adhesion additives mentioned in the present disclosure have osmotic pressures that are much lower than urea, and therefore have less influence on physiological tissues.

Preservation Condition Test for Hydrogel Composition

Example 31

1.5 parts by weight of vancomycin and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition. Next, the preservation time and form of the hydrogel composition were tested at room temperature, and the results are shown in Table 2. Then, the hydrogel composition was ground and then dissolved in water and the dissolving time thereof was determined, and was tested to determine whether it was capable of gelling under 37° C. or not, and the results are shown in Table 2. According to Table 2, it is known that the hydrogel composition which is dissolved after being lyophilized is still temperature-sensitive.

Example 32

1.25 parts by weight of vancomycin and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition. Next, the preservation time and form of the hydrogel composition were tested at room temperature, and the results are shown in Table 2. Then, the hydrogel composition was ground and then dissolved in water and the dissolving time thereof was determined, and was tested to determine whether it was capable of gelling under 37° C. or not, and the results are shown in Table 2. According to Table 2, it is known that the hydrogel composition which is dissolved after being lyophilized is still temperature-sensitive.

Example 33

1 parts by weight of vancomycin and 15 parts by weight of the hydrogel of Hydrogel preparation example 1 were mixed well to obtain a mixture. The mixture was frozen under −15° C. to become a frozen mixture. Finally, a lyophilization process (pressure: 8 mTorr; continued for 2 days) was performed on the obtained frozen mixture under −20° C. to obtain a hydrogel composition. Next, the preservation time and form of the hydrogel composition were tested at room temperature, and the results are shown in Table 2. Then, the hydrogel composition was ground and then dissolved in water and the dissolving time thereof was determined, and was tested to determine whether it was capable of gelling under 37° C. or not, and the results are shown in Table 2. According to Table 2, it is known that the hydrogel composition which is dissolved after being lyophilized is still temperature-sensitive.

TABLE 2

| Hydrogel composition | Dissolving time (minute) | Preservation time and form (Room temperature) | Gelling under 37° C. |
|---|---|---|---|
| 15 parts by weight of Hydrogel + 1.5 parts by weight of Vancomycin | 15 | 6 months/soft sheet | Yes |

TABLE 2-continued

| Hydrogel composition | Dissolving time (minute) | Preservation time and form (Room temperature) | Gelling under 37° C. |
|---|---|---|---|
| 15 parts by weight of Hydrogel + 1.25 parts by weight of Vancomycin | 15 | 6 months/soft sheet | Yes |
| 15 parts by weight of Hydrogel + 1 parts by weight of Vancomycin | 15 | 6 months/soft sheet | Yes |

According to Table 2, it is known that the hydrogel compositions obtained from Examples 31-33 of the present disclosure can be rapidly dissolved after being added to water and is convenient for use, and the preservation time thereof can be as long as 6 months. In addition, the hydrogel compositions which have been dissolved in water are capable of gelling under 37° C., and thus when the composition is applied inside the body of a warm-blooded animal, the hydrogel composition will convert into gel form at a specific region and will not slide, and can achieve an anti-adhesion effect to prevent tissue adhesion and protect the tissues. Therefore, the hydrogel compositions of the present disclosure are highly suited for use as a temperature-sensitive hydrogel material.

Test for Solution Form-Gel Form

Example 34

Based on FIG. 1, it is known that the temperature for converting a solution form of 5-15 parts by weight of the hydrogel of Hydrogel preparation example 1 mixed with 0.1-0.5 parts by weight of hyaluronic acid into a gel form is between 36° C. and 50° C., and that proved that the hydrogel compositions of the present disclosure are temperature-sensitive under 37° C. and are capable of gelling.

Evaluation of Anti-Adhesion Effect

Example 35

A female C57BL mouse (7-8 weeks old, 25-30 g weight) was injected with an anesthetic (Zoletil/40 mg/kg) and a muscle relaxant (Ropum 10 mg/kg) through intraperitoneal injection. After the mouse was completely anesthetized, the hairs on the belly were shaved and the abdominal cavity was opened. The ovaries on the two sides were sewn on the corresponding sides of the abdominal cavity with 5/0 sutures, respectively. 30 μl hydrogel composition (0.25 parts by weight of hyaluronic acid+15 parts by weight of the hydrogel of Hydrogel preparation example 1) was injected into the abdominal cavity. After that, the abdominal cavity was sutured with 4/0 sutures. After the surgery was completed, the mouse was placed on a 37° C. heater plate to prevent hypothermia. After the anesthetic wore off, the mouse was placed back in the cage, and the condition of the adhesion was observed after 7 days and 14 days. The results are shown in Table 3.

Comparative Example 3 (Control Group)

A female C57BL mouse (7-8 weeks old, 25-30 g weight) was injected with an anesthetic (Zoletil/40 mg/kg) and a muscle relaxant (Ropum 10 mg/kg) through intraperitoneal injection. After the mouse was completely anesthetized, the hairs on the belly were shaved and the abdominal cavity was opened. The ovaries on the two sides were sewn on the corresponding sides of the abdominal cavity with 5/0 sutures, respectively. 30 μl 5% bleach was injected into the abdominal cavity. After that, the abdominal cavity was sutured with 4/0 sutures. After the surgery was completed, the mouse was placed on a 37° C. heater plate to prevent hypothermia. After the anesthetic wore off, the mouse was placed back in the cage, and the condition of the adhesion was observed after 7 days and 14 days. The results are shown in Table 3.

Comparative Example 4 (Control Group)

A female C57BL mouse (7-8 weeks old, 25-30 g weight) was injected with an anesthetic (Zoletil/40 mg/kg) and a muscle relaxant (Ropum 10 mg/kg) through intraperitoneal injection. After the mouse was completely anesthetized, the hairs on the belly were shaved and the abdominal cavity was opened. The ovaries on the two sides were sewn on the corresponding sides of the abdominal cavity with 5/0 sutures, respectively. A film (0.8×0.8 cm) (commodity name: Seprafilm; manufacture: Genzyme) was placed into the abdominal cavity. After that, the abdominal cavity was sutured with 4/0 sutures. After the surgery was completed, the mouse was placed on a 37° C. heater plate to prevent hypothermia. After the anesthetic wore off, the mouse was placed back in the cage, and the condition of the adhesion was observed after 7 days and 14 days. The results are shown in Table 3.

Comparative Example 5 (Control Group)

A female C57BL mouse (7-8 weeks old, 25-30 g weight) was injected with an anesthetic (Zoletil/40 mg/kg) and a muscle relaxant (Ropum 10 mg/kg) through intraperitoneal injection. After the mouse was completely anesthetized, the hairs on the belly were shaved and the abdominal cavity was opened. The ovaries on the two sides were sewn on the corresponding sides of the abdominal cavity with 5/0 sutures, respectively. 30 μl hydrogel of Hydrogel preparation example 1 was injected into the abdominal cavity. After that, the abdominal cavity was sutured with 4/0 sutures. After the surgery was completed, the mouse was placed on a 37° C. heater plate to prevent hypothermia. After the anesthetic wore off, the mouse was placed back in the cage, and the condition of the adhesion was observed after 7 days and 14 days. The results are shown in Table 3.

Comparative Example 6 (Control Group)

A female C57BL mouse (7-8 weeks old, 25-30 g weight) was injected with an anesthetic (Zoletil/40 mg/kg) and a muscle relaxant (Ropum 10 mg/kg) through intraperitoneal injection. After the mouse was completely anesthetized, the hairs on the belly were shaved and the abdominal cavity was opened. The ovaries on the two sides were sewn on the corresponding sides of the abdominal cavity with 5/0 sutures, respectively. 30 μl 58 KDa hyaluronic acid was injected into the abdominal cavity. After that, the abdominal cavity was sutured with 4/0 sutures. After the surgery was completed, the mouse was placed on a 37° C. heater plate to prevent hypothermia. After the anesthetic wore off, the mouse was placed back in the cage, and the condition of the adhesion was observed after 7 days and 14 days. The results are shown in Table 3.

Clinically, the adhesion level ranges from Level 0 to Level 3. Level 0 means no adhesion. Level 1 means that there is a mist-like film on the organ while it can be pricked and separated easily, and for the extent of adhesion, 1-30% adhesion occurs on surrounding organs. Level 2 means that there are connections between organs through connective tissues and a stronger force is required for separating the organs, and for the extent of adhesion, 31-70% adhesion occurs on surrounding organs. Level 3 means that the tissues and the peritoneal cavity adhere to each other, seriously, and they cannot be easily separated, and for the extent of adhesion, 71-100% adhesion occurs on surrounding organs.

TABLE 3

| | Adhesion score |
|---|---|
| Example 35 | 0 |
| Comparative example 3 (Control group) | 2 |
| Comparative example 4 (Control group) | 0 |
| Comparative example 5 (Control group) | 1 |
| Comparative example 6 (Control group) | 0.67 |

Based on Table 3, it is known that by using the hydrogel composition of the present disclosure, after an abdominal cavity open type surgery, no adhesion occurs, and the anti-adhesion effect of the hydrogel composition of the present disclosure is as good as that of the commercial product (Comparative example 4).

Accordingly, the hydrogel composition of the present disclosure has a temperature-sensitive effect, and compared to traditional bio-hydrogels and film dressings, has following significant advantages.

The hydrogel composition of the present disclosure is in a solution form under room temperature, and while being injected into an animal body, it will present a gel form due to the body temperature and form a barrier protection layer, and that helps to reduce adhesion occurring after a surgery. Compared to commercial products, the hydrogel composition of the present disclosure has the same anti-adhesion effect. Although commercial products have good anti-adhesion effects, they still have problems when being placed in a precise position (due to the sliding of the film product). On the contrary, the hydrogel composition of the present disclosure can rapidly gel through being injected or placed in a specific position, and form a protective barrier to reduce the harm due to adhesion which occurs after a surgery. In addition, the hydrogel composition of the present disclosure can be stably preserved for 6 months under room temperature, and still has gelling properties under 37° C. after being re-dissolved. The hydrogel composition of the present disclosure is more suitable for use in a minimally invasive surgery.

It will be apparent to those skilled in the art that various modifications and variations can be made to the disclosed embodiments. It is intended that the specification and examples be considered as exemplary only, with the true scope of the disclosure being indicated by the following claims and their equivalents.

What is claimed is:

1. A hydrogel composition, comprising:
a hydrogel having a structure represented by Formula (I) or Formula (II) shown as follows:

A-B-BOX-B-A,      Formula (I);

B-A-B-(BOX-BAB)n-BOX-B-A-B,      Formula (II), wherein, the polymer block A is polyethylene glycol (PEG) or methoxy-poly(ethylene glycol) (mPEG), the polymer block B is a hydrophobic polyester polymer, BOX is a bifunctional group monomer of 2, 2'-Bis(2-oxazoline) for coupling di-block of A-B or tri-block of B-A-B, and n is an integer greater than or equal to 0; and
hyaluronic acid,
wherein a weight ratio of the hyaluronic acid to the hydrogel is 0.05-0.1:3, and
wherein the hydrogel composition has an anti-adhesion effect and is temperature sensitive.

2. The hydrogel composition as claimed in claim 1, wherein the polymer block B comprises poly(lactide-co-glycolide) (PLGA), poly(propionic-co-lactic) (PPLA), poly(valeric-co-lactic) (PVLA) or poly(caproic-co-lactic) (PCLA).

3. The hydrogel composition as claimed in claim 1, wherein the hydrogel composition is powder.

4. The hydrogel composition as claimed in claim 3, wherein a particle size of the powder is between 0.1 μm and 1 mm.

5. A method of making a gel, comprising:
dissolving the hydrogel composition as claimed in claim 1 in water at a first temperature to form a liquid; and
applying the liquid to a substrate, wherein the substrate has a second temperature, and the liquid forms into a gel at the second temperature.

6. The method of making a gel as claimed in claim 5, wherein the first temperature is between 4° C. and 30° C.

7. The method of making a gel as claimed in claim 5, wherein a viscosity of the liquid is less than 100 Pa-s.

8. The method of making a gel as claimed in claim 5, wherein the second temperature is between 30° C. and 55° C.

9. The method of making a gel as claimed in claim 5, wherein a viscosity range of the gel is between 200 Pa-s and 250 Pa-s.

10. A hydrogel composition, comprising:
a hydrogel having a structure represented by Formula (I) or Formula (II) shown as follows:

A-B-BOX-B-A,      Formula (I);

B-A-B-(BOX-BAB)n-BOX-B-A-B,      Formula (II), wherein, the polymer block A is polyethylene glycol (PEG) or methoxy-polyethylene glycol) (mPEG), the polymer block B is a hydrophobic polyester polymer, BOX is a bifunctional group monomer of 2,2'-Bis(2-oxazoline) for coupling di-block of A-B or tri-block of B-A-B, and n is an integer greater than or equal to 0; and
an anti-adhesion additive,
wherein the anti-adhesion additive comprises glucose, poly(vinyl alcohol) (PVA) or poly(ethylene glycol) diacrylate (PEGDA) and
wherein the anti-adhesion additive is glucose and a weight ratio of the anti-adhesion additive to the hydrogel is 0.02-0.1:3, or wherein the anti-adhesion additive is poly(vinyl alcohol) (PVA) and a weight ratio of the anti-adhesion additive to the hydrogel is 0.12-6:3, or wherein the anti-adhesion additive is poly(ethylene glycol)diacrylate (PEGDA) and a weight ratio of the anti-adhesion additive to the hydrogel is 0.01-6:3, and
wherein the hydrogel composition has an anti-adhesion effect and is temperature-sensitive.

\* \* \* \* \*